United States Patent
Onyebuagu et al.

(10) Patent No.: US 9,149,660 B2
(45) Date of Patent: Oct. 6, 2015

(54) COMPOSITION AND METHOD FOR CREAM BLEACH PRODUCT

(75) Inventors: William Onyebuagu, Englishtown, NJ (US); Mabel Covey, Englishtown, NJ (US); Christine Brieva, Englishtown, NJ (US); Osman Lambiro, Englishtown, NJ (US)

(73) Assignee: Hair Systems Inc., Englishtown, NJ (US)

( * ) Notice: Subject to any disclaimer, the term of this patent is extended or adjusted under 35 U.S.C. 154(b) by 0 days.

(21) Appl. No.: 12/989,881

(22) PCT Filed: Apr. 29, 2009
(Under 37 CFR 1.47)

(86) PCT No.: PCT/US2009/042099
§ 371 (c)(1),
(2), (4) Date: Oct. 27, 2010

(87) PCT Pub. No.: WO2009/134875
PCT Pub. Date: Nov. 5, 2009

(65) Prior Publication Data
US 2011/0038818 A1     Feb. 17, 2011

Related U.S. Application Data

(60) Provisional application No. 61/048,706, filed on Apr. 29, 2008.

(51) Int. Cl.
| | |
|---|---|
| *A61Q 5/08* | (2006.01) |
| *A61K 8/92* | (2006.01) |
| *A61Q 5/12* | (2006.01) |
| *A61K 8/04* | (2006.01) |
| *A61K 8/23* | (2006.01) |
| *A61K 8/81* | (2006.01) |

(52) U.S. Cl.
CPC . *A61Q 5/08* (2013.01); *A61K 8/042* (2013.01); *A61K 8/23* (2013.01); *A61K 8/8117* (2013.01); *A61K 8/92* (2013.01)

(58) Field of Classification Search
None
See application file for complete search history.

(56) References Cited

U.S. PATENT DOCUMENTS

| | | | |
|---|---|---|---|
| 5,888,484 A | 3/1999 | Schmitt et al. | |
| 6,365,136 B1 * | 4/2002 | Lauscher et al. | 424/62 |
| 2004/0076594 A1 | 4/2004 | Legrand | |
| 2004/0181883 A1 * | 9/2004 | Legrand et al. | 8/405 |
| 2005/0028833 A1 | 2/2005 | Christine Vena et al. | |
| 2006/0078524 A1 | 4/2006 | Midha et al. | |
| 2007/0033744 A1 | 2/2007 | Kravtchenko | |
| 2007/0251538 A1 | 11/2007 | Ghannad et al. | |
| 2009/0095315 A1 | 4/2009 | De La Mettrie et al. | |

FOREIGN PATENT DOCUMENTS

| | | |
|---|---|---|
| DE | 29923409 U1 | 8/2000 |
| WO | 9416672 A1 | 8/1994 |
| WO | 2005048959 A1 | 6/2005 |

OTHER PUBLICATIONS

Stedman's Online, "Mineral Oil Definition", http://www.stedmansonline.com/content.aspx?id=mlrM0900007383&termtype=t, accessed Aug. 7, 2012.*

* cited by examiner

*Primary Examiner* — Bethany Barham
*Assistant Examiner* — Melissa Javier
(74) *Attorney, Agent, or Firm* — Blank Rome LLP

(57) ABSTRACT

This invention relates to compositions and methods for hair bleaching. In particular, the invention concerns stabilized hair bleach products that contain at least one persulfate salt, and an oil gel. The composition of the present invention forms an emulsion where the oil and salt do not separate providing a consistent and stable hair bleach formulation.

11 Claims, No Drawings

COMPOSITION AND METHOD FOR CREAM BLEACH PRODUCT

This application claims the priority of U.S. Provisional Application Ser. No. 61/048,706, filed Apr. 29, 2008, which is incorporated herein by reference.

FIELD OF THE INVENTION

This invention relates to compositions and methods for hair bleaching. In particular, the invention concerns stabilised hair bleach products that contain a persulfate salt and an oil gel.

BACKGROUND OF THE INVENTION

Hair bleaching is a well-known process in the hair cosmetic field. Hair bleaching involves the application of an oxidizing agent to the hair for a period of time effective to achieve a desired lighter hair shade. The oxidizing agent typically is a hydrogen peroxide solution in concentrations ranging from 6 to 12% by weight. The hydrogen peroxide is applied to the hair under alkaline pH conditions and gradually lightens the shade of the hair by oxidizing the melanin that gives it color.

To enhance the lightening efficacy of the peroxide solution, a persulfate salt-based formulation may be incorporated as a "booster". The sodium, potassium or ammonium persulfate salt is provided as a powder, which is mixed with the hydrogen peroxide solution prior to use. The mixed product is then applied to the hair for a period of time effective to achieve the desired lighter hair shade.

Currently, hair bleaches are most commonly found in the two-component kit form. One component comprises an aqueous-based hydrogen peroxide composition containing solution or emulsion. The second component comprises a powdered bleach composition that contains persulfate salts and alkaline agent(s), which act as accelerators of the bleaching process when the two components are combined. This powdered bleach composition may be used alone to bleach hair or in combination with an aqueous hydrogen peroxide composition. The hydrogen peroxide and persulfates are very reactive when combined and form nascent oxygen in addition to hydrogen and sodium sulfide. The nascent oxygen greatly facilitates oxidizing and bleaching of melanin from the hair.

The salts and other active ingredients (such as alkaline agents) routinely originate as a powdery mixture of ingredients which are then transformed into a paste by mixing with water or other liquid. The powdery mixture often has the disadvantage of dusting. The oxidizing and alkaline agents in the powdery mixture may be harmful if ingested or inhaled; therefore, it is desirable to obtain a hair bleach that does not cause this dusting.

De-dusted formulations have been developed to control or reduce the dusting in powdered bleaching compositions. The de-dusted formulation generally mixes the powder with at least a basic oil, such as mineral oil or ethyldexyl pelargonate, resulting in a cream-type formulation. Typically, these prior art chemical systems are either unstable (causing separation of the oil and the salt phases) or too waxy and, therefore, cosmetically un-appealing after premature formula separation due to the presence of oils and salts. The separation has the effect that different portions of the same batch of powder taken from different locations in the batch have different chemical compositions and thus may provide a different bleaching effect.

There is a desire and a long-standing need to overcome these disadvantages of the current technology with regards to controlled hair bleaching with a cream formulation. The primary challenge in developing a cream bleach resides in the need to develop a formulation that contains the necessary salt concentration level within a small oil matrix, which remains consistent enough to be cosmetically appealing and desirable to hair and scalp application with minimum damage, and has almost no physical separation of the components.

SUMMARY OF THE INVENTION

An object of this invention is to create a stable and homogeneous hair bleaching composition which shows no separation as commonly seen in benchmark formulations. Since these extreme high salt formulations require anhydrous environments, the challenge is to successfully create a stable cream-like suspension which does not separate or harden upon aging. Currently marketed products either show oil separation or become hardened and dry within months of fabrication.

It is, therefore, an object of this invention to provide a stable composition, preferably a homogeneous composition, for hair bleaching which imparts a long-lasting bleaching property to the hair fiber, while at the same time substantially eliminating exposure to potentially environmental damage from formula separation.

Another object of the present invention is to provide a formula matrix utilizing combinations of organic solvents, salts, fillers and active salts such as persulfates of sodium, potassium and ammonium.

Still another object of the present invention is to utilize ingredients such as the following: oil gels, persulfates, waxes, silicates, metasilicates, carbomers, silica, oxides, and/or chelating agents to create a creamy or paste composition for bleaching head hair.

Yet another object of this invention is to provide a method of applying a controlled cream base onto hair and scalp.

Finally, another object of this invention is to provide salons and consumers a more consistent and stable hair bleaching composition as a better substitute for the current market cream bleach as well as other dusty and de-dusted powdered bleach compositions in use. This, in turn, provides consumers with a much safer application method and environment.

DETAILED DESCRIPTION OF THE PREFERRED EMBODIMENTS

The present invention relates to a new cream bleach composition utilizing an oil gel as a suspension medium for persulfate salts to create a stable suspension/emulsion system with minimal to no separation in comparison to current market standards. The present invention provides a stable emulsion that allows for a better mixing and application on a client's hair with reduced damage during the process. It also represents a dust-free product, making it environmentally friendly and controlled at the point of use. The oil gel contains a hydrophobic and lipophilic material, and a polymer/copolymer. The hydrophobic and lipophilic material is preferably an oil, and more preferably an emollient. In a preferred embodiment, the hydrophobic and lipophilic material is a hydrocarbon. In a preferred embodiment, the polymer/copolymer forms a gel in which the hydrophobic and lipophilic material is suspended. Optionally, the composition may further contain silica, a chelating agent, a conditioner, and/or a thickening agent. Preferably, the concentration of oil gel is about 5 to 60%, preferably 30 to 45% (by weight), and the total persulfate salts concentration is about 25 to 90%, preferably 55 to 70% (by weight).

The present invention utilizes host-guest molecule vehicles to transport the active ingredients of persulfates to their bleaching sites on the cuticle. The vehicle used by the present invention is the oil gel while the active ingredients are the persulfates. The oil gel contains at least one hydrophilic and lipophilic material, and at least one polymer/copolymer in the form of a gel. The invention uses the oil gel in hair cream bleach formulations as a vehicle (suspending agent) for the persulfate's active ingredients, while at the same time preventing the separation of the salt and the oil phases by uniformly suspending them in a medium. The oil gel vehicle may be Versagels or Synergels by Penreco or other substitute vendors or manufacturers of similar chemistry concept. The Versagel series includes the following:

Versagel C-series
Versagel M-series
Versagel P-series
Versagel R-series

The preferred formulations utilize the M-series Versagels as the oil gel vehicle, but the other series are also useful in the present invention. The M-series includes, but not limited to, the following:

Versagel M (mineral oil and ethylene/propylene/styrene copolymer and butylene/ethylene/styrene copolymer)
Versagel ME (hydrogenated polyisobutene and ethylene/propylene/styrene copolymer and butylene/ethylene/styrene copolymer)
Versagel ML (alkyl benzoate and ethylene/propylene/styrene copolymer and butylene/ethylene/styrene copolymer)
Versagel MP (isopropyl palmitate and ethylene/propylene/styrene copolymer and butylene/ethylene/styrene copolymer)
Versagel MC (isohexadecane and ethylene/propylene/styrene copolymer and butylene/ethylene/styrene copolymer)
Versagel MD (isododecane and ethylene/propylene/styrene copolymer and butylene/ethylene/styrene copolymer)
Versagel MN (isononyl isononanoate and ethylene/propylene/styrene copolymer and butylene/ethylene/styrene copolymer)

The oil gels can be made using methods described in U.S. Pat. No. 5,221,534, which is incorporated herein by reference. The preferred hydrophobic and lipophilic materials are selected from mineral oil, hydrogenated polyisobutene, alkyl benzoate, isopropyl palmitate, isohexadecane, isododecane, and isononyl isononanoate. The preferred polymer/copolymer is ethylene/propylene/styrene copolymer and butylene/ethylene/styrene copolymer.

The persulfate salt contains one or more of various alkaline earth metals, alkali metals, or ammonium persulfate compounds that exhibit oxidizing activity (generating active oxygen) when combined with the aqueous oxidizing agent composition. Preferably such persulfates comprise one or more of an alkali metal, alkaline earth metal, or ammonium persulfate. Examples of alkali metal persulfates include lithium, sodium, potassium, cesium, and the like. Examples of suitable alkaline earth metals include magnesium, calcium, and the like. Particularly preferred are sodium, potassium, and ammonium persulfates. The persulfates are generally in particulate form, having particle sizes ranging from about 0.1 to 200 microns.

A preferred embodiment utilizes gelled mineral oils (containing mineral oils and polymers/copolymers) and is able to provide complete emulsification, thereby providing a very stable environment for the incorporation of persulfate salts. This provides a very uniform and homogeneous application during the bleaching of human head hair without separation of the mineral oil and the persulfates.

In an alternative embodiment, the present invention may contain just one or two of the active persulfates and may be ammonia free if the ammonium persulfate is not utilized.

The composition of the present invention may further include one or more conditioning agents, chelating agents, thickeners, and/or silica. Conditioning agents are added to the composition in order to soften and provide a more luxurious look. Useful hair conditioning agents include, but are not limited to, laurol lysine and/or aloe vera powder. Useful chelating agents include, but are not limited to, ethylenediaminetetraacetic acid (EDTA), disodium EDTA, tetrasodium EDTA, cyclodextrin, sodium citrate, tetrasodium pyrophosphate, disodium pyrophosphate, and mixtures thereof. Useful thickeners include, but are not limited to, aluminum sterate, magnesium sterate, calcium sterate, sodium sterate, algin, kaolin, guar gum, xanthan gum, beeswax, acrylates/C10-30 alkyl acrylate crosspolymer, carbomers, hydroxyethyl cellulose, hydroxypropylmethyl cellulose, carboxymethyl cellulose, and mixtures thereof.

Preferred compositions of the present invention include:
A) 30%-70% persulfate salts, 3%-20% silicates, and 5%-60% oil gel;
B) 25%-70% potassium persulfate, 2%-20% sodium silicate/metasilicates, and 10%-50% oil gel;
C) Sodium Persulfaate Salt=25%-70% sodium persulfate, 2%-20% sodium silicate/metasilicates, and 10%-50% oil gel;
D) 25%-50% ammonium persulfate, 2%-20% sodium silicate/metasilicates, and 10%-50% oil gel;
E) 25%-70% potassium persulfate, 25%-70% sodium persulfate, 2%-20% sodium silicate/metasilicates, and 10%-50% oil gel;
F) 25%-70% potassium persulfate, 5%-20% ammonium persulfate, 2%-20% sodium silicate/metasilicates, and 10%-50% oil gel; and
G) 25%-70% sodium persulfate, 5%-20% ammonium persulfate, 2%-20% sodium silicate/metasilicates, and 10%-50% oil gel.

The emulsification of the oil gel and persulfate salts plus additional supporting ingredients to produce a finished cream bleach formula for the head hair can be easily maintained with a great amount of comfort and satisfaction. The present invention provides a technology to maintain a stable chemical product to bleach hair to desired satisfaction, by maintaining formula stability and uniformity without separation, thereby eliminating bleaching inconsistency. There is currently no known bleaching cream with similar consistency without showing separation over time.

The present formulation preferably is used in combination with an oxygen donor, such as hydrogen peroxide, to bleach hair. In use, the formulation can be mixed with hydrogen peroxide before being applied to the hair. Once mixed with peroxide, it should be applied within about ten (10) minutes. The formulation may be applied to the hair with any number of application devices, with the primary purpose of scarcely or densely depositing the bleach lotion to the hair to achieved the desired result.

Without further description, it is believed that one of ordinary skill in the art can, using the preceding description and the following illustrative examples, make and utilize the compositions of the present invention and practice the claimed methods. The following examples are given to illustrate the present invention. It should be understood that the invention is not to be limited to the specific conditions or details described in these examples.

EXAMPLE 1

Formulations

Cream bleach compositions were made in accordance with the following formulas A to F:

| Cream Bleach Formula A | |
|---|---|
| Component | %(W/W) |
| Potassium Persulfate | 25.500-40.000 |
| Mineral oil (and) Ethylene/Propylene/Styrene Copolymer (and) Butylene/Ethylene/Styrene Copolymer | 10.000-23.700 |
| Mineral Oil | 2.000-7.000 |
| Ammonium Persulfate | 1.000-5.000 |
| Sodium Persulfate | 1.000-5.000 |
| Sodium Metasilicate | 0.500-5.000 |
| Sodium Silicate | 0.500-5.000 |
| Acrylates/C10-30 Alkyl Acrylate Crosspolymer | 0.500-3.000 |
| C 12-15 Alkyl Benzoate | 0.500-2.000 |
| Magnesium Oxide | 0.100-1.000 |
| Beeswax | 0.100-0.500 |
| Ozokerite Wax | 0.100-0.500 |
| Silica | 0.100-0.500 |
| Titanium Dioxide | 0.100-0.500 |
| Acrylates Copolymer (and) Silica | 0.100-0.500 |
| Fragrance | 0.100-0.300 |
| Sodium Magnesium Silicate | 0.050-0.200 |
| Disodium EDTA | 0.050-0.200 |
| Lauroyl Lysine | 0.010-0.050 |
| *Aloe Barbadensis* Leaf Juice | 0.010-0.050 |

| Cream Bleach Formula B | |
|---|---|
| Component | %(W/W) |
| Potassium Persulfate | 45.180-70.00 |
| Mineral oil (and) Ethylene/Propylene/Styrene Copolymer (and) Butylene/Ethylene/Styrene Copolymer | 24.675-50.00 |
| Mineral Oil | 7.000-30.00 |
| Ammonium Persulfate | 5.000-20.00 |
| Sodium Persulfate | 5.000-40.00 |
| Sodium Metasilicate | 5.000-20.00 |
| Sodium Silicate | 5.000-20.000 |
| Acrylates/C10-30 Alkyl Acrylate Crosspolymer | 3.000-7.00 |
| Ethyl Hexyl Pelargonate | 2.000-15.00 |
| Magnesium Oxide | 1.000-5.00 |
| Beeswax | 0.500-3.00 |
| Ozokerite Wax | 0.500-3.00 |
| Silica | 0.500-3.00 |
| Titanium Dioxide | 0.500-5.00 |
| Acrylates Copolymer (and) Silica | 0.500-5.00 |
| Fragrance | 0.300-1.00 |
| Sodium Magnesium Silicate | 0.200-1.00 |
| Disodium EDTA | 0.200-1.00 |
| Lauroyl Lysine | 0.050-2.00 |
| *Aloe Barbadensis* Leaf Juice | 0.050-0.50 |
| Ultramarine Blue | 0.009-0.10 |

| Cream Bleach Formula C | |
|---|---|
| Component | %(W/W) |
| Potassium Persulfate | 20.000-39.691 |
| Mineral oil (and) Ethylene/Propylene/Styrene Copolymer (and) Butylene/Ethylene/Styrene Copolymer | 10.000-25.000 |
| Mineral Oil | 2.000-7.000 |
| Ammonium Persulfate | 1.000-5.000 |
| Sodium Persulfate | 1.000-5.000 |
| Sodium Metasilicate | 1.000-5.000 |
| Sodium Silicate | 1.000-5.000 |
| Acrylates/C10-30 Alkyl Acrylate Crosspolymer | 0.500-3.000 |
| C 12-15 Alkyl Benzoate | 1.000-2.000 |
| Magnesium Oxide | 0.200-1.000 |
| Beeswax | 0.200-0.500 |
| Ozokerite Wax | 0.200-0.500 |
| Silica | 0.300-0.500 |
| Titanium Dioxide | 0.200-0.500 |
| Acrylates Copolymer (and) Silica | 0.200-0.500 |
| Fragrance | 0.100-0.300 |
| Sodium Magnesium Silicate | 0.100-0.200 |
| Disodium EDTA | 0.100-0.200 |
| Lauroyl Lysine | 0.010-0.050 |
| *Aloe Barbadensis* Leaf Juice | 0.010-0.050 |
| Ultramarine Blue | 0.001-0.0085 |
| Total | |

| Cream Bleach Formula D | |
|---|---|
| Component | %(W/W) |
| Potassium Persulfate | 40.000-50.000 |
| Mineral oil (and) Ethylene/Propylene/Styrene Copolymer (and) Butylene/Ethylene/Styrene Copolymer | 21.000-50.000 |
| Mineral Oil | 10.400-20.000 |
| Ammonium Persulfate | 5.000-20.000 |
| Sodium Persulfate | 5.000-50.000 |
| Sodium Metasilicate | 4.000-20.000 |
| Sodium Silicate | 4.000-25.000 |
| Acrylates/C10-30 Alkyl Acrylate Crosspolymer | 4.000-7.000 |
| C 12-15 Alkyl Benzoate | 3.000-20.000 |
| Magnesium Oxide | 1.000-10.000 |
| Beeswax | 0.500-5.000 |
| Ozokerite Wax | 0.500-5.000 |
| Silica | 0.500-5.000 |
| Titanium Dioxide | 0.500-10.000 |
| Acrylates Copolymer (and) Silica | 0.500-8.000 |
| Fragrance | 0.300-2.000 |
| Sodium Magnesium Silicate | 0.200-5.000 |
| Disodium EDTA | 0.200-2.000 |
| Lauroyl Lysine | 0.050-10.000 |
| *Aloe Barbadensis* Leaf Juice | 0.050-2.000 |

| Cream Bleach Formula E | |
|---|---|
| Component | %(W/W) |
| Potassium Persulfate | 65.000-45.000 |
| Mineral oil (and) Ethylene/Propylene/Styrene Copolymer (and) Butylene/Ethylene/Styrene Copolymer | 50.000-23.700 |
| Mineral Oil | 25.000-7.000 |
| Sodium Persulfate | 2.000-5.000 |
| Sodium Metasilicate | 2.000-5.000 |
| Sodium Silicate | 2.000-5.000 |
| Acrylates/C10-30 Alkyl Acrylate Crosspolymer | 1.000-3.000 |
| Ethyl Hexyl Pelargonate | 0.500-2.000 |
| Magnesium Oxide | 0.200-1.000 |
| Beeswax | 0.200-0.500 |
| Ozokerite Wax | 0.200-0.500 |
| Silica | 0.100-0.500 |
| Titanium Dioxide | 0.100-0.500 |
| Acrylates Copolymer (and) Silica | 0.100-0.500 |
| Fragrance | 0.100-0.300 |
| Sodium Magnesium Silicate | 0.050-0.200 |
| Disodium EDTA | 0.100-0.200 |
| Lauroyl Lysine | 0.010-0.050 |
| *Aloe Barbadensis* Leaf Juice | 0.010-0.050 |

| Cream Bleach Formula F | |
|---|---|
| Component | %(W/W) |
| Potassium Persulfate | 10.000-70.000 |
| Mineral oil (and) Ethylene/Propylene/Styrene Copolymer (and) Butylene/Ethylene/Styrene Copolymer | 5.000-50.000 |
| Mineral Oil | 5.000-20.000 |
| Ammonium Persulfate | 5.000-20.000 |
| Sodium Persulfate | 5.000-65.000 |
| Sodium Metasilicate | 5.000-15.000 |
| Sodium Silicate | 5.000-20.000 |
| Acrylates/C10-30 Alkyl Acrylate Crosspolymer | 1.000-10.000 |
| C 12-15 Alkyl Benzoate | 1.000-10.000 |
| Magnesium Oxide | 1.000 |
| Beeswax | 0.500 |
| Ozokerite Wax | 0.500 |
| Silica | 0.500 |
| Titanium Dioxide | 0.500 |
| Acrylates Copolymer (and) Silica | 0.500 |
| Fragrance | 0.300 |
| Sodium Magnesium Silicate | 0.200 |
| Disodium EDTA | 0.200 |
| Lauroyl Lysine | 0.050 |
| *Aloe Barbadensis* Leaf Juice | 0.050 |

EXAMPLE 2

Stability

Cream bleach compositions were made and tested for their pH, active oxygen, viscosity, and stability (resistance to separation) over time. The following tables summarize the results (except where noted, viscosities are measured as is with spindle 7 @ 2.5 PRM):

| Stability Results for Cream Cream Bleach Formula A (pilot batch) | | | | | | | |
|---|---|---|---|---|---|---|---|
| | | pH | | Active | Viscosity | Viscosity | Separation |
| Environment | Interval | 1% | Alkalinity | Oxygen | Tube | Jar | Yes | No |
| 40 deg. | Initial | 10.54 | 1.10 | 1.26 | 421000 | 421000 | | X |
| | 1 month | 10.36 | 1.22 | 2.71 | 500000 | 534000 | | X |
| | 3 months | 10.47 | 0.69 | 2.12 | 616000 | 613000 | | X |
| | 6 months | 10.47 | 0.96 | 2.85 | 686000 | 774000 | | X |
| | 9 months | | | | | | | |
| | 1 year | | | | | | | |
| RT | 1 month | 10.47 | 1.46 | 2.45 | 429000 | 483000 | | X |
| | 3 months | 10.46 | 1.12 | 2.36 | 478000 | 546000 | | X |
| | 6 months | 10.43 | 1.29 | 2.59 | 562000 | 714000 | | X |
| | 9 months | | | | | | | |
| | 1 year | | | | | | | |
| Ref | 1 month | 10.44 | 1.33 | 2.76 | 454000 | 488000 | | X |
| | 3 months | 10.49 | 0.87 | 2.01 | 469000 | 426000 | | X |
| | 6 months | 10.54 | 1.17 | 2.88 | 520000 | 651000 | | X |
| | 9 months | | | | | | | |
| | 1 year | | | | | | | |
| Freeze | 1 month | 10.40 | 1.35 | 2.91 | 418000 | 454000 | | X |
| | 3 months | 10.66 | 0.93 | 2.44 | 462000 | 488000 | | X |
| | 6 months | 10.52 | 1.22 | 2.71 | 459000 | 646000 | | X |
| | 9 months | | | | | | | |
| | 1 year | | | | | | | |

| Stability Results for Cream Bleach Formula E | | | | | | |
|---|---|---|---|---|---|---|
| Environment | Interval | pH 1% | Alkalinity | Active Oxygen | Viscosity | Separation Yes | No |
| | Initial | 11.25 | 1.878 | 2.696 | 454000 | | X |
| 40 deg. | 3 months | 11.11 | 1.61 | 2.75 | 440000 | | X |
| | 6 months | 11.25 | 1.75 | 2.60 | 887000 | | X |
| | 9 months | 11.31 | 1.66 | 2.45 | 805000 | | X |
| | 1 year | 11.11 | 1.52 | 2.31 | 621000 | | X |
| RT | 3 months | 10.99 | 1.8 | 2.70 | 315000 | | X |
| | 6 months | 11.10 | 1.82 | 2.80 | 669000 | | X |
| | 9 months | 11.11 | 1.75 | 2.79 | 422000 | | X |
| | 1 year | 10.97 | 1.74 | 2.89 | 472000 | | X |
| Ref | 3 months | 11.25 | 1.71 | 2.60 | 376000 | | X |
| | 6 months | 11.35 | 1.85 | 2.77 | 674000 | | X |
| | 9 months | 11.52 | 1.90 | 2.65 | 456000 | | X |
| | 1 year | 11.62 | 2.02 | 2.71 | 555000 | | X |
| Freeze | 3 months | 11.20 | 1.88 | 2.65 | 398000 | | X |
| | 6 months | 11.10 | 1.96 | 2.7 | 659000 | | X |
| | 9 months | 11.21 | 1.95 | 2.67 | 416000 | | X |
| | 1 year | 11.29 | 1.88 | 2.66 | 498000 | | X |

| Stability Results for Cream Bleach Formula A (lab batch) | | | | | | |
|---|---|---|---|---|---|---|
| Environment | Interval | pH 1% | Alkalinity | Active Oxygen | Viscosity | Separation Yes | No |
| | Initial | 11.24 | 1.933 | 1.755 | 478000 | | X |
| 40 deg. | 3 months | 11.10 | 1.88 | 2.15 | 453000 | | X |
| | 6 months | 11.21 | 1.78 | 2.22 | 887000 | | X |
| | 9 months | 11.01 | 1.80 | 2.45 | 698000 | | X |
| | 1 year | 10.87 | 1.79 | 2.63 | 725000 | | X |
| RT | 3 months | 11.15 | 1.99 | 2.20 | 429000 | | X |
| | 6 months | 11.0 | 2.05 | 2.21 | 605000 | | X |

Stability Results for Cream Bleach Formula A (lab batch)

| Environment | Interval | pH 1% | Alkalinity | Active Oxygen | Viscosity | Separation Yes | Separation No |
|---|---|---|---|---|---|---|---|
| | 9 months | 11.11 | 1.95 | 2.35 | 451000 | | X |
| | 1 year | 10.94 | 2.01 | 2.44 | 536000 | | X |
| Ref | 3 months | 10.99 | 2.10 | 2.10 | 366000 | | X |
| | 6 months | 11.10 | 2.01 | 2.25 | 688000 | | X |
| | 9 months | 11.20 | 1.90 | 2.40 | 482000 | | X |
| | 1 year | 10.89 | 2.0 | 2.65 | 560000 | | X |
| Freeze | 3 months | 11.25 | 1.95 | 2.15 | 469000 | | X |
| | 6 months | 11.18 | 2.10 | 2.35 | 656000 | | X |
| | 9 months | 11.05 | 1.99 | 2.65 | 469000 | | X |
| | 1 year | 10.81 | 1.89 | 2.80 | 613000 | | X |

Stability Results for Cream Bleach Formula B

| Environment | Interval | pH 1% | Alkalinity | Active Oxygen | Viscosity | Separation Yes | Separation No |
|---|---|---|---|---|---|---|---|
| | Initial | 11.24 | 1.25 | 2.44 | 229000 | | X |
| 40 deg. | 3 months | 11.10 | 1.30 | 2.45 | 160000 | | X |
| | 6 months | 11.01 | 1.40 | 2.55 | 238000 | | X |
| | 9 months | 10.99 | 1.45 | 2.66 | 259000 | | X |
| | 1 year | 10.85 | 1.70 | 2.59 | 264000 | | X |
| RT | 3 months | 10.95 | 1.41 | 2.50 | 166000 | | X |
| | 6 months | 10.99 | 1.55 | 2.66 | 235000 | | X |
| | 9 months | 11.10 | 1.70 | 2.71 | 205000 | | X |
| | 1 year | 10.95 | 2.0 | 2.77 | 190000 | | X |
| Ref | 3 months | 11.11 | 1.45 | 2.65 | 138000 | | X |
| | 6 months | 10.95 | 1.50 | 2.51 | 234000 | | X |
| | 9 months | 10.95 | 1.35 | 2.44 | 202000 | | X |
| | 1 year | 10.91 | 1.28 | 2.26 | 198000 | | X |
| Freeze | 3 months | 11.00 | 1.40 | 2.55 | 197000 | | X |
| | 6 months | 10.95 | 1.33 | 2.56 | 274000 | | X |
| | 9 months | 10.99 | 1.50 | 2.50 | 204000 | | X |
| | 1 year | 10.90 | 1.48 | 2.70 | 195000 | | X |

Stability Results for Cream Bleach Formula C

| Environment | Interval | pH 1% | Alkalinity | Active Oxygen | Viscosity | Separation Yes | Separation No |
|---|---|---|---|---|---|---|---|
| | Initial | 10.47 | 1.176 | 2.762 | 163000 | | X |
| 40 deg. | 3 months | 10.57 | 1.30 | 2.70 | 157000 | | X |
| | 6 months | 10.61 | 1.45 | 2.77 | 248000 | | X |
| | 9 months | 10.75 | 1.66 | 2.71 | 214000 | | X |
| | 1 year | 10.98 | 1.90 | 2.66 | 222000 | | X |
| RT | 3 months | 10.60 | 1.25 | 2.65 | 112000 | | X |
| | 6 months | 10.65 | 1.28 | 2.69 | 211000 | | X |
| | 9 months | 10.80 | 1.35 | 2.51 | 189000 | | X |
| | 1 year | 10.89 | 1.35 | 2.40 | 171000 | | X |
| Ref | 3 months | 10.75 | 1.25 | 2.61 | 141000 | | X |
| | 6 months | 10.70 | 1.40 | 2.55 | 208000 | | X |
| | 9 months | 10.66 | 1.44 | 2.50 | 202000 | | X |
| | 1 year | 10.80 | 1.50 | 2.53 | 176000 | | X |
| Freeze | 3 months | 10.70 | 1.20 | 2.66 | 117000 | | X |
| | 6 months | 10.88 | 1.35 | 2.50 | 198000 | | X |
| | 9 months | 10.89 | 1.42 | 2.66 | 284000 | | X |
| | 1 year | 11.12 | 1.43 | 2.78 | 163000 | | X |

Stability Results for Cream Bleach Formula D

| Environment | Interval | pH 1% | Alkalinity | Active Oxygen | Viscosity* | Separation Yes | Separation No |
|---|---|---|---|---|---|---|---|
| | Initial | 10.35 | 1.017 | 3.125 | 213000 | | X |
| 40 deg. | 3 months | 10.25 | 1.21 | 3.0 | 181000 | | X |
| | 6 months | 10.30 | 1.32 | 3.26 | 204000 | | X |
| | 9 months | 10.31 | 1.29 | 3.10 | 171000 | | X |
| | 1 year | 10.25 | 1.35 | 2.92 | 193000 | | X |
| RT | 3 months | 10.26 | 1.15 | 3.11 | 152000 | | X |
| | 6 months | 10.30 | 1.21 | 2.95 | 182000 | | X |
| | 9 months | 10.40 | 1.20 | 2.90 | 165000 | | X |
| | 1 year | 10.39 | 1.23 | 2.80 | 171000 | | X |
| Ref | 3 months | 10.45 | 1.25 | 2.99 | 156000 | | X |
| | 6 months | 10.60 | 1.36 | 2.85 | 182000 | | X |
| | 9 months | 10.66 | 1.45 | 2.66 | 182000 | | X |
| | 1 year | 10.89 | 1.88 | 2.68 | 185000 | | X |
| Freeze | 3 months | 10.30 | 1.26 | 3.10 | 170000 | | X |
| | 6 months | 10.30 | 1.21 | 3.15 | 189000 | | X |
| | 9 months | 10.40 | 1.11 | 3.20 | 182000 | | X |
| | 1 year | 10.37 | 1.16 | 3.06 | 169000 | | X |

*Viscosity is measured as is with spindle 6 @ 2.5 RPM.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A stable hair bleach composition comprising about 5-60% by weight of the composition of an oil gel and about 25-90% by weight of the composition of a persulfate salt, wherein the oil gel contains mineral oil, ethylene/propylene/styrene copolymer, and butylene/ethylene/styrene copolymer.

2. The hair bleach composition of claim 1 wherein the persulfate salt is selected from the group consisting of sodium persulfate, potassium persulfate, and ammonia persulfate.

3. The hair bleach composition of claim 1, further comprising a chelating agent, a conditioner, a thickener, or silica.

4. A method for bleaching hair comprising the step of applying the composition of claim 1 to the hair.

5. The method of claim 4, where in the composition is mixed with hydrogen peroxide before the application to the hair.

6. A method for making a stable hair bleach composition comprising the steps of a) providing an oil gel, wherein the oil gel contains mineral oil, ethylene/propylene/styrene copolymer, and butylene/ethylene/styrene copolymer; and b) suspending a persulfate salt in the oil gel, wherein the concentration of the persulfate salt is about 25-90% by weight of the composition and the concentration of the oil gel is about 5-60% by weight of the composition.

7. The method of claim 6, wherein the persulfate salt is selected from the group consisting of sodium persulfate, potassium persulfate, and ammonia persulfate.

8. The method of claim 6, further comprising a step of suspending a chelating agent, a conditioner, a thickener, or silica in the oil gel.

9. The method claim 6, wherein the persulfate salt is selected from the group consisting of sodium persulfate, potassium persulfate, and ammonia persulfate.

10. A method for preventing separation of a composition containing a hydrophobic and lipophilic material and a persulfate salt, said method comprising the step of suspending the hydrophobic and lipophilic material and the persulfate salt in a polymer/copolymer gel, wherein the hydrophobic and lipophilic material is mineral oil and the polymer/copolymer gel is ethylene/propylene/styrene copolymer and butylene/ethylene/styrene copolymer, wherein the concentration of the persulfate salt is about 25-90% by weight of the composition and the concentration of the oil gel is about 5-60% by weight of the composition.

11. The method of claim 10, wherein the persulfate salt is selected from the group consisting of sodium persulfate, potassium persulfate, and ammonia persulfate.

\* \* \* \* \*